United States Patent [19]

Johnson et al.

[11] Patent Number: 4,585,894

[45] Date of Patent: Apr. 29, 1986

[54] PROCESS FOR PRODUCING 9-CARBAMOYL FLUORENE DERIVATIVES

[75] Inventors: Derek Johnson; Alan C. Spreadbury, both of Warrington, England

[73] Assignee: Eli Lilly and Company, Indianapolis, Ind.

[21] Appl. No.: 543,648

[22] Filed: Oct. 19, 1983

[51] Int. Cl.$^4$ ............... C07C 102/00; C07C 103/28
[52] U.S. Cl. ................................. 564/164
[58] Field of Search ....................... 564/164

[56]  References Cited

U.S. PATENT DOCUMENTS

| 4,197,313 | 4/1980 | Lacefield et al. | 424/304 |
| 4,277,495 | 7/1981 | Lacefield et al. | 424/309 |
| 4,282,170 | 8/1981 | Lavagnino et al. | 260/465 D |
| 4,382,093 | 5/1983 | Lacefield et al. | 424/324 |
| 4,452,745 | 6/1984 | Lacefield et al. | 564/164 X |
| 4,486,592 | 12/1984 | Lacefield et al. | 564/164 X |

OTHER PUBLICATIONS

Buehler et al., *Survey of Organic Syntheses*, pp. 424–425, Wiley–Interscience (1970).

Wagner et al., *Synthetic Organic Chemistry*, p. 662, Wiley and Sons, Ltd., (1953).

*Primary Examiner*—Thomas A. Waltz
*Attorney, Agent, or Firm*—Charles W. Ashbrook; Arthur R. Whale

[57]  ABSTRACT

Processes are described for preparing pharmaceutical 9-carbamoyl-9-aminoalkylfluorenes and intermediates in their preparation.

4 Claims, No Drawings

PROCESS FOR PRODUCING 9-CARBAMOYL FLUORENE DERIVATIVES

BACKGROUND OF THE INVENTION

A group of 9-disubstituted fluorenes recently has been discovered to have potent antiarrhythmic activity; see U.S. Pat. Nos. 4,197,313 and 4,382,093. The 9-carbamoyl-9-aminoalkylfluorenes are among the most active compounds, and one compound within this group, namely 9-(3-isopropylaminopropyl)9-carbamoylfluorene hydrochloride, is now known generically as indecainide. The reported synthesis of the 9-carbamoyl-9-aminoalkylfluorenes have included acid hydrolysis of 9-cyano-9-aminoalkylfluorene, and more recently reductive alkylation of a 9-carbamoyl-9-cyanoalkylfluorene, see U.S. Pat. No. 4,282,170.

An object of the invention is to provide a process for the preparation of such 9-carbamoyl-9-aminoalkylfluorenes which is convenient to use, gives good yields and can be conducted under relatively mild conditions.

The invention provides a process for producing a compound of the formula

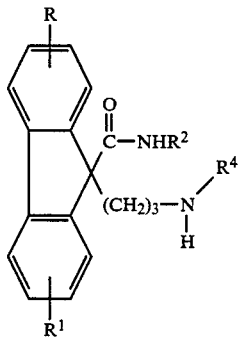

(I)

wherein

R and $R^1$ independently are hydrogen, $C_1$-$C_4$ alkyl or halo;

$R^2$ is hydrogen or $C_1$-$C_6$ alkyl; and $R^4$ is hydrogen, $C_1$-$C_6$ alkyl, —$CH_2C_2$-$C_5$ alkenyl or phenyl $C_1$-$C_3$ alkyl; or a salt thereof;

which comprises reacting a compound of the formula

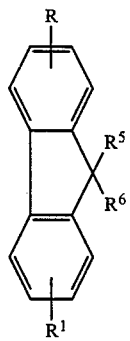

(II)

wherein

R and $R^1$ are as defined above; and either $R^5$ is —$CONHR^2$ where $R^2$ is as defined above and $R^6$ is —$(CH_2)_2CHO$;

or $R^5$ and $R^6$, together, form the ring

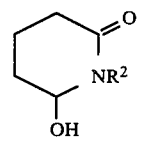

with an amine of the formula $R^4NH_2$ and a reducing agent, or isolating an intermediate of the following formula from reaction of the compound of formula (II) with amine:

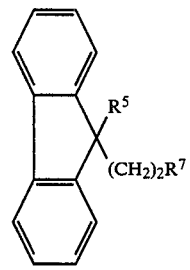

(III)

where $R^7$ is —CH(OH)$NHR^4$ or —CH=$NR^4$ and reducing the said intermediate.

The compounds of formula (II) are of two types:

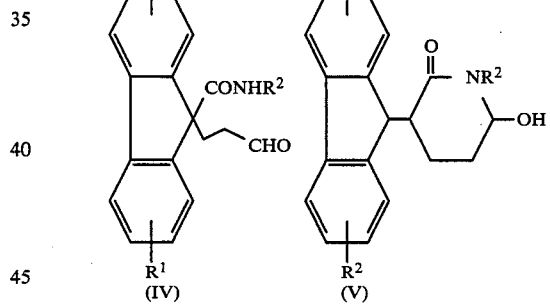

Such compounds are in fact interchangeable since reaction of base on compound (V) readily yields the aldehyde of formula (IV). In most systems an equilibrium between the two forms exists and the reactive species in the above process of the invention is probably always of formula (IV). Notwithstanding this both species can be employed in the reaction. Amine ($R^4NH_2$) and reducing agent can be added simultaneously or the reducing agent added after reaction with amine.

The compounds of formula (III) are products of the reaction of amine with the compound of formula (II) and can be isolated and subsequently reacted with reducing agent. Often, however, it is preferable to avoid the extra step of isolating the intermediate product and to carry out the reaction in situ as described above.

In a further aspect of the invention compounds of formulae (II) can be prepared by a process which comprises reacting a compound of the formula

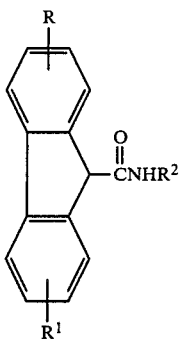

with acrolein (CH$_2$=CHCHO) under basic conditions.

Thus the invention also provides a process for preparing a compound of formula (I) as defined above, which comprises (a) reacting a compound of the formula

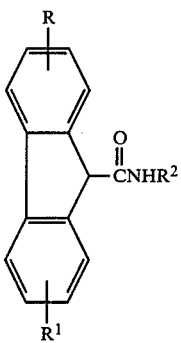

wherein R, R$^1$ and R$^2$ are as defined above, with acrolein under basic conditions to provide a compound of formula

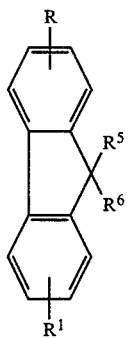

(II)

wherein R$^5$ and R$^6$ are as defined above, and (b) reacting the compound of formula (II) with an amine of the formula R$^4$NH$_2$ and a reducing agent.

DETAILED DESCRIPTION OF THE INVENTION

In the above formulas, R and R$^1$ define substituents on the fluorene aromatic rings. The substituents can be hydrogen, C$_1$-C$_4$ alkyl such as methyl, ethyl, isopropyl, tert.-butyl and the like, or halo such as fluoro, chloro, bromo or iodo. Preferred compounds are those wherein R and R$^1$ both are hydrogen.

R$^2$ in the above formulas defines a substituent on the carbamoyl nitrogen atom and includes hydrogen and C$_1$-C$_6$ alkyl such as methyl, ethyl, n-propyl, n-butyl, 2-methylpentyl, iso-pentyl and the like. Preferred compounds of the invention are those wherein R$^2$ is hydrogen.

In the above formulas R$^4$ is C$_1$-C$_6$ alkyl, CH$_2$C$_2$-C$_5$ alkenyl or phenyl-C$_1$-C$_3$ alkyl. The term "C$_1$-C$_6$ alkyl" carries its art recognized meaning and includes methyl, isopropyl, tert.-butyl, and 1,1-dimethylbutyl. A particularly preferred R$^4$ alkyl group is isopropyl. "CH$_2$C$_2$-C$_5$ Alkenyl" refers to groups such as allyl, 3-hexenyl, 4-pentenyl and the like. The term "phenyl-C$_1$-C$_3$ alkyl" includes benzyl, 2-phenylethyl and 3-phenylpropyl.

The reaction of amine with the compound of formula (II) above, is one of amination and, in the case where an intermediate is not isolated, the reaction is one of reductive amination. It is preferably carried out with approximately equimolar quantities of the reactants or with an excess of the amine, at a pH within the range of 6 to 10, such as for example 8 to 9, and at a temperature of from −20° C. to 100° C., such as for example from 25° C. to 80° C. It is preferred to perform the reaction under basic conditions which may be ensured by the use of a molar excess of the amine reactant. The subsequent reduction in the case where an intermediate is isolated is carried out under similar conditions.

Suitable reducing agents for use in the above process can be catalytic or chemical. Examples of the former kind include hydrogenation with palladium and charcoal, hydrogen and Adams catalyst (PtO$_2$), and platinum on charcoal. Such catalytic methods of hydrogen are discussed for instance in "Practical Catalytic Hydrogenation" by M. Freifelder, Wiley Interscience, 1971, and in "Catalytic Hydrogenation in Organic Synthesis" by P. N. Rylander, Academic Press, 1979. Chemical reagents which may preferably be used include, for example, sodium cyanoborohydride, lithium cyanoborohydride, tetrabutylammonium cyanoborohydride. The first named reagent, which is the most preferred for use in the process of the invention, is reviewed, for example, in the paper by C. F. Lane, Aldrichimica Acta 1975, 8, 3. Reducing agents with too strong an effect should be avoided.

The reaction is generally carried out in an inert organic solvent and we have found that acetonitrile, dichloromethane and ethyl acetate are particularly useful for this purpose but other solvents can be employed such as for example tetrahydrofuran and aromatic and halogenated hydrocarbons, or if desired the amine reactant can be employed in sufficient quantity to serve both as reactant and solvent. The products can be extracted by routine procedures.

As noted above compounds of formula (II) can be prepared by a novel process which comprises reaction with acrolein according to the following scheme

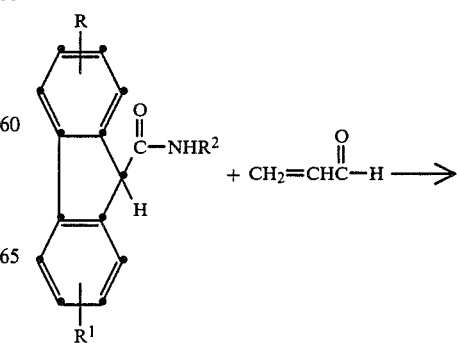

-continued

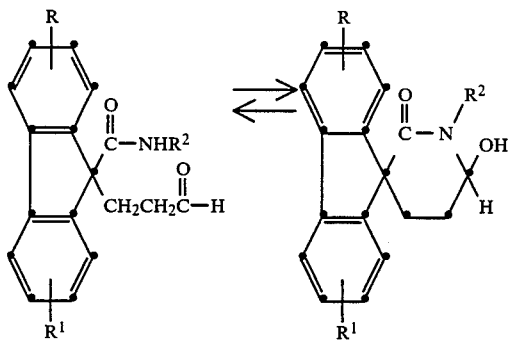

where R, R[1] and R[2] are as defined above. The reaction is carried out by combining the 9-carbamoylfluorene with acrolein in approximately equimolar quantities in the presence of a base. The particular base employed and the quantity are not critical, and an equimolar quantity or excess generally is used. Typical bases that can be employed include organic bases such as benzyltrimethyl ammonium hydroxide (Triton B), triethylamine, as well as alkali metal hydrides such as sodium hydride. The reaction is preferably conducted in an organic solvent, and typical solvents include ethers such as diethyl ether and tetrahydrofuran, and aromatics such as benzene and toluene. The reaction typically is carried out at a temperature of about 0° to about 100° C., and at such temperature is usually complete within about one to about eight hours. The product of the reaction, a tautomeric mixture of an aldehyde and a cyclic carbinol, is readily isolated by removing the reaction solvent or when a water-miscible solvent has been employed, by dilution of the reaction mixture with water. The product can be crystallized from common solvents such as for example ethyl acetate or ether, when it is obtained predominantly in the carbinol form (formula (V) which as such can be readily isolated.

The following detailed Examples further illustrate the processes provided by this invention.

EXAMPLE 1

6'-Hydroxyspiro(9H-fluorene-9,3'-piperidine)-2'-one

A solution of 10.0 g (48 mM) of 9-carbamoylfluorene in 100 ml of tetrahydrofuran was heated at 45° C. and stirred under a nitrogen blanket while 2 ml of N-benzyltrimethyl ammonium hydroxide (Triton B) were added in one portion. The reaction mixture was stirred for fifteen minutes at 45° C., and then 2.8 g (50 mM) of acrolein were added dropwise over ten minutes. The reaction mixture was heated at reflux for three hours following the addition. The reaction mixture was cooled to room temperature and concentrated to an oil by evaporation of the solvent under reduced pressure. The oil was dissolved in 100 ml of ethyl acetate and washed with water. The organic layer was dried and the solvent was removed by evaporation to provide a solid. The solid was crystallized from ethyl acetate and petroleum ether to give 4.0 g of solid product. The product was purified further by high pressure liquid chromatography over silica gel, eluting with chloroform containing 5% (v/v) methanol. The appropriate fractions were combined and concentrated to dryness to afford 500 mg of 6'-hydroxyspiro(9H-fluorene-9,3'-piperidine)-2'-one melting at 210°–212° C.

Analysis calculated for $C_{17}H_{15}NO_2$ (after drying at 120° C.) Theory: 76.96; H, 5.70; N, 5.28; O, 12.06. Found: 76.66; H, 5.99; N, 5.21; O, 12.27

Mass Spec. M+ Theory 265, Found 265.

NMR (DMSOd$_6$): δ 1.6–2.5 (m, 4H); 5.32 (broad s, 1H): 6.12 (d, 1H); 7.3–8.1 (m, 8H); 8.32 (d, 1H).

IR (KBr): 1642 cm$^{-1}$ (amide)

EXAMPLE 2

6'-Hydroxyspiro(9H-fluoroene-9,3'-piperidine)-2'-one

Following the general procedure of Example 1, 20.9 g (0.1 mole) of 9-carbamoylfluorene were added to 300 ml of tetrahydrofuran. The solution was heated to 50° C. and stirred while 6 ml of benzyltrimethylammonium hydroxide were added in one portion. After stirring the reaction mixture at 50° C. for thirty minutes, 6.2 g (0.11 mole) of acrolein were added and the mixture was then heated at reflux for four hours. The reaction mixture was cooled to 25° C. and the solvent was removed by evaporation under reduced pressure to provide 29.9 g of 6'-hydroxyspiro(9H-fluorene-9,3'-piperidine)-2'-one and its tautomeric isomer 9-carbamoyl-9-(3-oxopropyl)fluorene, m.p. 199°–201° C.

Analysis (after drying at 120° C. for one minute) Calculated for $C_{16}H_{15}NO_2$. Theory: C, 76.96; H, 5.70; N, 5.28. Found: C, 76.71; H, 5.88; N, 5.23.

Mass Spec. M+ Theory 265; Found 265.

NMR (CDCl$_3$+DMSOd$_6$): δ 1.7–2.6 (m, 4H); 5.3 (broad s, 1H); 5.9 (d, 1H); 7.2–7.9 (m, 9H).

IR (KBr): 1639 cm$^{-1}$ (amide)

EXAMPLE 3

6'-Hydroxyspiro(9H-fluorene-9,3'-piperidine)-2'-one

A solution of N-benzyltrimethylammonium hydroxide (Triton B) which is a 40% methanolic solution (3.5 ml) in acetonitrile (10 ml) was added dropwise over 0.25 hour to a suspension of 9-carbamoylfluorene (20.9 g) in acetonitrile (100 ml) keeping the temperature below 25° C. The reaction mixture was stirred at room temperature for 2 hours. Water (300 ml) was then added slowly over 1 hour and the crystallised product was isolated by filtration, washed with water and dried in vacuo overnight at 50° C. 89%, melting point 201°–205° C. (decomp). The product was identical spectroscopically to that prepared in Example 1.

EXAMPLE 4

9-Carbamoyl-9-(3-isopropylaminopropyl)fluorene hydrochloride

A solution of isopropylamine (45.0 ml) in acetonitrile (250 ml) was cooled to 10° C. and hydrogen chloride gas introduced into the solution keeping the temperature below 15° C. to pH 8.5±0.3. The resultant slurry was allowed to warm to room temperature and sodium cyanoborohydride (12.0 g) added in one portion and the pH readjusted to 8.5 if necessary. 6'-Hydroxyspiro-(9H-fluorene-9,3'-piperidine)-2'-one (30.0 g) was then added and the reaction mixture heated to reflux for 2 hours. The mixture was allowed to cool to room temperature and dilute hydrochloride acid added to pH 1–2 to destroy any excess cyanoborohydride. The acetonitrile was removed under reduced pressure and the residue basified with sodium hydroxide solution (pH 11) and extracted with dichloromethane (3×100 ml) and the combined organic layers washed with sodium hydroxide solution, dried with anhydrous sodium sulphate and evaporated to give the crystalline free amine.

This amine was dissolved in acetone (120 ml) and cooled to 15° C. Dry hydrogen chloride gas was passed through the solution until a pH of 7 was obtained. The resultant mixture was cooled slowly to −30° C., and the product isolated by filtration, washed with cold acetone, and dried in vacuo at 40° C. overnight to give the title compound.

NMR (DMSOd$_6$): δ 1.08 (s, 3H); 1.19 (s, 3H); 2.2–2.9 (m, 6H); 6.28 (s, 1H); 7.0 (s, 1H); 7.3–8.1 (m, 9H); 8.8 (broad s, 2H).

EXAMPLE 5

9-Carbamoyl-9-(3-isopropylaminopropyl)fluorene

6'-Hydroxyspiro-(9H-fluorene-9,3'-piperidine)-2'-one (2.7 g) was dissolved in isopropylamine (350 ml) and 10% palladium on charcoal (0.3 g) was added and the vessel pressurised to 90 p.s.i. with hydrogen. The reaction mixture was then heated at 40° C. for 16 hours and then allowed to cool to room temperature. The catalyst was removed by filtration and the isopropylamine evaporated under reduced pressure. The resulting residue was dissolved in dichloromethane (20 ml) washed with water (2×50 ml), dried with anhydrous sodium sulphate and evaporated to dryness under reduced pressure. The residue was triturated with hexane to give the title compound as white crystals, the identity of which was confirmed by thin layer chromatographic comparison with an authentic sample (silica gel, ethylacetate:-methanol 80:20 v/v).

EXAMPLE 6

9-Carbamoyl-9-(3-isopropyliminopropyl)fluorene

A mixture of 5.9 g (0.1 mole) of isopropylamine and 2.5 g (0.009 mole) of the tautomeric mixture from Example 2 was stirred at 25° C. under a nitrogen blanket for sixteen hours. Excess isopropylamine was removed by evaporation under reduced pressure to provide, following crystallization from ethyl acetate and petroleum ether, 0.7 g of a solid identified as 9-carbamoyl-9-(3-isopropyliminopropyl)fluorene, m.p. 149°–155° C.

M+ theory 306; found 306.

NMR (CDCl$_3$): signals at δ 1.0 (two s, 6H); 1.62 (M, 2H); 2.65 (M, 2H); 3.06 (M, 1H); 5.05 (Broad s, 2H, signal removed with D20 shake); 7.28–7.79 (M, 9H).

EXAMPLE 7

9-Carbamoyl-9-(3-isopropylaminopropyl)fluorene hydrochloride

9-Carbamoyl-9-(3-isopropyliminopropyl)fluorene prepared as described in Example 6, was dissolved in 200 ml of ethanol containing 3.0 g of 5% palladium on carbon. The reaction mixture was shaken in an hydrogen atmosphere at 25° C. for six hours. The actual hydrogen uptake was 19.5 lbs; theoretical uptake was 19.7 lbs. The reaction mixture was filtered to remove the hydrogenation catalyst and the filtrate was concentrated to dryness by evaporation under reduced pressure. The solid that was formed was dissolved in 100 ml of diethyl ether containing 100 ml of ethyl acetate. The product was extracted into 6N hydrochloric acid and the acid extracts were combined, cooled to 10° C. and made alkaline to pH 10.0 by addition of 10% (w/v) aqueous sodium hydroxide. The alkaline solution was extracted several times with fresh diethyl ether, and the ethereal extracts were combined, washed with water, dried, and then saturated with gaseous hydrogen chloride. The precipitate which formed was collected by filtration and recrystallized from ethanol and diethyl ether to give 2.1 g of 9-carbamoyl-9-(3-isopropylaminopropyl)fluorene hydrochloride (indecainide hydrochloride), m.p. 206°–207.5° C.

Analysis calculated for C$_{20}$H$_{25}$ClN$_2$O. Theory: C, 69.65; H, 7.31; H, 8.12. Found: C, 69.55; H, 7.18; N, 7.99.

IR (KBr): 1680, 1665 cm$^{-1}$

NMR (DMSOd$_6$): δ 1.08 (s, 3H); 1.19 (s, 3H); 2.2–2.9 (m, 6H); 6.28 (s, 1H); 7.0 (s, 1H); 7.3–8.1 (m, 9H); 8.8 (broad s, 2H).

Titration (66% v/v N,N-dimethylformamide-water) pKa=10.2.

We claim:

1. A process for producing a compound of the formula

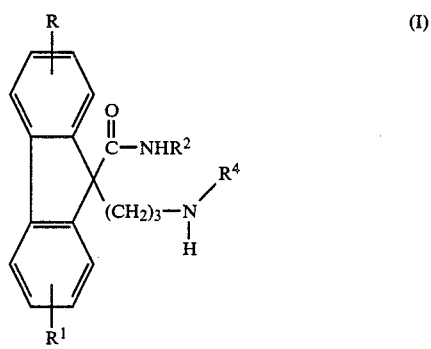

wherein
R and R$^1$ independently are hydrogen, C$_1$–C$_4$ alkyl or halo;
R$^2$ is hydrogen or C$_1$–C$_6$ alkyl; and
R$^4$ is hydrogen, C$_1$–C$_6$ alkyl, —CH$_2$C$_2$–C$_5$ alkenyl or phenyl C$_1$–C$_3$ alkyl; or a salt thereof;
which comprises reacting a compound of the formula

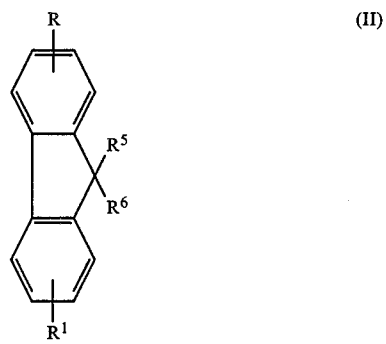

wherein
R and R$^1$ are as defined above; and
R$^5$ and R$^6$, together, form the ring

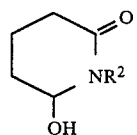

with an amine of the formula R⁴NH₂ and a reducing agent, or isolating from reaction of the compound of formula (II) with amine, an intermediate of formula

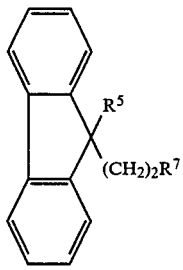
(III)

where $R^7$ is —CH(OH)NHR⁴ or —CH=NR⁴ and reducing the said intermediate.

2. A process according to claim 1 for preparing a compound of formula (I) in which R, $R^1$ and $R^2$ are hydrogen.

3. A process according to claim 2 for preparing a compound of formula (I) in which $R^4$ is isopropyl.

4. A process for preparing a compound of formula (I)

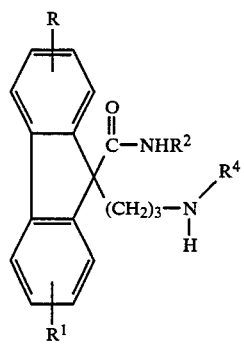
(I)

wherein
R and $R^1$ independently are hydrogen, $C_1$-$C_4$ alkyl or halo;

$R^2$ is hydrogen or $C_1$-$C_6$ alkyl; and
$R^4$ is hydrogen, $C_1$-$C_6$ alkyl, —CH₂C₂-C₅ alkenyl or phenyl $C_1$-$C_3$ alkyl; or a salt thereof;
which comprises
(a) reacting a compound of the formula

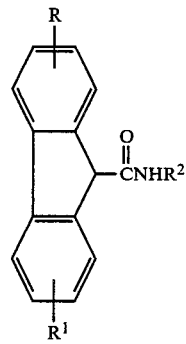

wherein
R, $R^1$ and $R^2$ are as defined in claim 1, with acrolein under basic conditions to provide a compound of formula

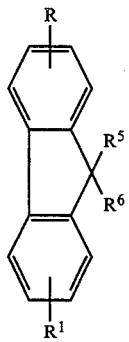
(II)

wherein $R^5$ and $R^6$ are as defined in claim 1, and
(b) reacting the resulting compound with an amine of the formula R⁴NH₂ and a reducing agent.

* * * * *